(12) United States Patent
Wirtz et al.

(10) Patent No.: US 10,185,015 B2
(45) Date of Patent: Jan. 22, 2019

(54) HANDHELD OSCILLATION APPLICATOR FOR USE IN A MAGNETIC RESONANCE RHEOLOGY IMAGING SYSTEM

(71) Applicant: KONINKLIJKE PHILIPS N.V., Eindhoven (NL)

(72) Inventors: Daniel Wirtz, Eindhoven (NL); Peter Mazurkewitz, Eindhoven (NL); Christoph Leussler, Eindhoven (NL); Peter Vernickel, Eindhoven (NL)

(73) Assignee: Koninklijke Philips N.C., Eindhoven (NL)

( * ) Notice: Subject to any disclaimer, the term of this patent is extended or adjusted under 35 U.S.C. 154(b) by 296 days.

(21) Appl. No.: 15/111,868

(22) PCT Filed: Jan. 24, 2015

(86) PCT No.: PCT/EP2015/051423
§ 371 (c)(1),
(2) Date: Jul. 15, 2016

(87) PCT Pub. No.: WO2015/110616
PCT Pub. Date: Jul. 30, 2015

(65) Prior Publication Data
US 2016/0334484 A1    Nov. 17, 2016

(30) Foreign Application Priority Data

Jan. 24, 2014    (EP) ..................................... 14152371

(51) Int. Cl.
*A61B 5/055*    (2006.01)
*G01R 33/563*    (2006.01)
(Continued)

(52) U.S. Cl.
CPC .......... *G01R 33/563* (2013.01); *A61B 5/0051* (2013.01); *A61B 5/055* (2013.01); *G01R 33/28* (2013.01); *G01R 33/56358* (2013.01)

(58) Field of Classification Search
CPC ....... A61B 5/055; A61B 8/4494; A61B 8/469; A61B 5/0035; A61B 5/0051; A61B 8/4281; G01R 33/543; G01R 33/5608
See application file for complete search history.

(56) References Cited

U.S. PATENT DOCUMENTS 6,833,703 B2 * 12/2004 Sinkus ................... A61B 5/055
324/318
8,281,663 B2 * 10/2012 Ehman ............. G01R 33/56358
324/318
(Continued)

OTHER PUBLICATIONS

Muthipillai R, "Magnetic Resonance Imaging of Acoustic Strain Waves" Proc. Soc. Magn. Reson. 1, p. 189 (1995).
(Continued)

*Primary Examiner* — Alesa Allgood

(57) ABSTRACT

A handheld oscillation applicator (40) for use in a magnetic resonance rheology imaging system (10), for applying mechanical oscillations to at least a portion of a subject of interest (20), the handheld oscillation applicator (40) comprising a housing (54), at least one transducer unit (48) configured to output mechanical energy, a piston (68) that is mechanically linked to the at least one transducer unit (48), the piston (68) including a first end (70), a second end (72), and an opening (74) that extends between the first end (70) and the second end (72), wherein the housing (54) comprises at least one opening (60), and the at least one opening (60) of the housing (54) and the opening (74) of the piston (68) at least partially overlap with regard to a housing opening direction (66) defined by an opening center (62) of the opening (60) of the housing (54) at a first surface (56) and
(Continued)

an opening center (64) of the opening (60) of the housing (54) at a second surface (58); and an oscillation applicator system (38), including: a handheld oscillation applicator (40), a transducer driving unit (42) for energizing the at least one transducer unit (48), a sensing unit (50) configured to determine a physical quantity that is representative of an amplitude of mechanical oscillations being applied to at least the portion of the subject of interest (20), and to provide an output signal representing the determined physical quantity, at least one closed-loop control circuit for maintaining a mechanical displacement amplitude of the transducer unit (48) at a selected level, wherein the closed-loop control circuit is configured to provide an output signal for controlling the transducer driving unit (42), based on the output signal received from the sensing unit (50).

14 Claims, 4 Drawing Sheets

(51) Int. Cl.
   *A61B 5/00*     (2006.01)
   *G01R 33/28*    (2006.01)

(56) References Cited

U.S. PATENT DOCUMENTS

| | | | | |
|---|---|---|---|---|
| 8,305,076 | B2 * | 11/2012 | Sack | A61B 5/055 |
| | | | | 324/309 |
| 9,173,589 | B2 * | 11/2015 | Chen | A61B 5/055 |
| 2006/0293597 | A1 * | 12/2006 | Johnson | A61B 5/4312 |
| | | | | 600/437 |
| 2010/0005892 | A1 * | 1/2010 | Ehman | G01R 33/56358 |
| | | | | 73/644 |
| 2011/0006767 | A1 * | 1/2011 | Sack | A61B 5/055 |
| | | | | 324/309 |
| 2012/0259201 | A1 * | 10/2012 | Chen | A61B 5/055 |
| | | | | 600/411 |

OTHER PUBLICATIONS

Yeung, D, "MR Elastography of the Head and Neck: Driver Design and Initial Results" Magn. Reson. Imag., vol. 31 p. L 624-L 639 (2013).

Mariappan et al "Magnetic Resonance Elastography a Review" Clinical Anatomy, vol. 23, No. 6, Jun. 3, 2010 p. 497-511.

Tse et al, "Magnetic Resonance Elastography Hardware Design a Survey" Proceedings of HTE Institution of Mechanical Engineers, Journal of Engineering in Medicine, vol. 223, No. 4, May 1, 2009 p. 497-514.

Wang et al "On the Precision of Time of Flight Shear Wave Speed Estimation in Homogeneous Soft Solids . . . " IEEE Transactions on Ultrasonics Ferroelectrics and Frequency Control, vol. 60, No. 4, Apr. 1, 2013, p. 758-770.

Venkatesh et. al, Magnetic Resonance Elastography of Liver—Technique, Analysis, and Clinical Applications, JMRI 37, 544, 2013.

Glaser et. al, "Review of MR Elastography Applications and Recent Developments", JMRI, vol. 36, p. 757, 2012.

\* cited by examiner

HANDHELD OSCILLATION APPLICATOR FOR USE IN A MAGNETIC RESONANCE RHEOLOGY IMAGING SYSTEM

CROSS REFERENCE TO RELATED APPLICATIONS

This application is a U.S. national phase application of International Application No. PCT/EP2015/051423, filed on Jan. 24, 2015, which claims the benefit of EP Application Serial No. 14152371.2 filed on Jan. 24, 2014 and is incorporated herein by reference.

FIELD OF THE INVENTION

The invention pertains to an oscillation applicator and an oscillation applicator system for use in a magnetic resonance rheology imaging system.

BACKGROUND OF THE INVENTION

In the art of magnetic resonance imaging, it is known to characterize mechanical properties of human or animal tissue by magnetic resonance rheology (cf. for instance to Muthipillai R. et al., *Magnetic resonance imaging of acoustic strain waves*, Proc. Soc. Magn. Reson. Nice, 1:189, 1995). In magnetic resonance rheology, the tissue is driven to mechanically oscillate during magnetic resonance imaging, which leads to effects causing an imaging contrast due to differences in tissue viscosity or elasticity. Low-frequency mechanical waves are coupled into the tissue and are visualized via a magnetic resonance sequence. The obtained additional information can be used, for instance, to distinguish healthy from malign tissue.

A number of different mechanical transducers for applying the mechanical oscillations to the tissue have been proposed, such as electromagnetic designs, which make use of the main magnetic field $B_0$ inside the magnetic resonance scanner. Further, piezo-driven transducers or pneumatic designs were proposed for clinical application. In general, any mechanical transducer that appears to be suitable to the one skilled in the art may be employed.

Conventionally, magnetic resonance rheology examinations are carried out with a mechanical transducer that is statically attached to a subject of interest, for instance by strapping it around the subject of interest, or such that the subject of interest is lying on the mechanical transducer. An example of a conventional oscillation applicator for use in magnetic resonance rheology is shown in FIG. 5. The conventional oscillation applicator comprises a housing 96, which encompasses a mechanical transducer, and a piston 98 that is provided for transferring mechanical oscillations to the subject of interest. Dimensions of conventional oscillation applicators are about 50 millimeters in height with a footprint of about 100×100 mm².

Further, the paper '*MR elastography of the head and neck: Driver design and initial results*' by D. K. W. Yeung in Magn.Res.Imag. 31(2013)624-629 discloses a driver for MR elastography. This known driver comprises a tranducer embedded in a foam slab. The transducer has a protruding piston and a coil mounted at one of the piston. A headrest mould is positioned over the transducer and an opening opposing the centre of the piston is cut from the mould.

SUMMARY OF THE INVENTION

It is desirable to be able to apply mechanical oscillations to tissue of a subject of interest with a device that is optimized for a combination with interventional devices.

It is therefore an object of the invention to provide an oscillation applicator with improved performance and additional options regarding a combination with interventional applications, for use in a magnetic resonance rheology imaging system.

In one aspect of the present invention, the object is achieved by a handheld oscillation applicator for use in a magnetic resonance rheology imaging system, wherein the handheld oscillation applicator, upon activation, is configured for applying mechanical oscillations to at least a portion of a subject of interest to be imaged by the magnetic resonance rheology imaging system.

The handheld oscillation applicator comprises a housing, including at least a first surface that is configured to be arranged proximal to at least the portion of the subject of interest during applying mechanical oscillations, and at least a second surface that is configured to be arranged distal to at least a portion of the subject of interest during applying mechanical oscillations, at least one transducer unit that, upon being energized, is configured to output mechanical energy, a piston, which is mechanically linked to the at least one transducer unit, and is configured to transfer at least a part of the mechanical energy of the at least one transducer unit to at least the portion of the subject of interest to be imaged, the piston comprising a first end that is configured to be arranged proximal to at least the portion of the subject of interest during applying mechanical oscillations, wherein the first end of the piston is configured to be closer to the subject of interest than the first surface of the housing, a second end that is configured to be arranged distal to at least the portion of the subject of interest during applying mechanical oscillations, and an opening that extends between the first and the second end of the piston.

The housing comprises at least one opening extending between the first surface and the second surface. The at least one opening of the housing and the opening of the piston at least partially overlap with regard to a housing opening direction defined by a virtual connecting line between an opening center of the opening of the housing at the first surface and the center of the opening of the housing at the second surface. Accordingly, the overlap of the openings of the housing and of the piston form through-going openings.

The term "handheld", as used in this application, shall be understood particularly to imply a combination of physical properties, such as weight and size, of an object that allows for the object being held in hand by a physically average operator during use.

One advantage of the invention lies in that mechanical oscillations can be applied to at least the portion of the subject of interest from all sides with respect to an interventional device that is operated through the opening of the housing and the opening of the piston, so that the tissue-distinguishing properties of magnetic resonance rheology can be fully exploited at a location where it is needed most.

Another advantage of the invention lies in extended options of operating the oscillation applicator. For instance, the oscillation applicator can readily be adjusted by an interventionalist without interruption which is not possible with an oscillation applicator that is strapped to the subject of interest.

Yet another advantage of the invention lies in that the handheld oscillation applicator can readily be removed during an invention in order to provide more free moving space for the interventionalist.

The at least one transducer unit may be energized using electric energy. It may also be energized using mechanical energy that is generated remotely, and which may be transferred to the at least one transducer unit, for instance via a cardan mechanism or by hydraulic transmission.

Preferably, the first end of piston has a planar surface that lies in a plane that is arranged perpendicular to the housing opening direction.

In a preferred embodiment, a dimension of the overlap of the at least one opening of the housing and the opening of the piston perpendicular to the housing opening direction is at least 30 millimeters. More preferable, the dimension of the overlap is at least 40 millimeters, and, most preferable, at least 50 millimeters. By that, a large number of interventional devices can be operated through the clear space provided by the openings of the housing and the piston, and mechanical oscillations can be applied to at least the portion of the subject of interest from all sides with respect to these interventional devices.

In another preferred embodiment, an overall dimension of the housing and the piston in an operational state in a direction parallel to the housing opening direction is equal to or less than 45 millimeters. More preferable, the overall dimension of the housing and the piston is less than 40 millimeters, and, most preferable, less than 35 millimeters. In this way, the handheld oscillation applicator enables to operate an interventional device in a wide angular region with respect to the housing opening direction, if so required.

Preferably, at least one of the opening of the housing and the opening of the piston has an elliptical cross-section. The term "elliptical", as used in this application, shall be understood particularly to also encompass a circular cross-section. By that, the housing and the piston can be easily manufactured, and an appropriate cross-section of the clear space provided for operating interventional devices can be achieved.

In another preferred embodiment, the center of the opening in the first surface of the housing is offset from a geometric center of the first surface. The phrase "geometric center of the first surface", as used in this application, shall be understood particularly as the arithmetic mean position of all points of the first surface provided that the opening does not exist. In this way, a sufficient amount of housing area can be provided for the operator for conveniently holding the oscillation applicator while, at the same time, a dimension of the oscillation applicator in a direction perpendicular to the housing opening direction can still be kept compact.

In yet another preferred embodiment, the at least one transducer unit comprises two coaxially arranged coil members having windings that are connectable to a transducer driving unit for being provided with electrical energy. One of the coil members is directly or indirectly mechanically linked to the piston, and the common axis of the coil members coincides with the housing opening direction. A smallest distance between windings of each of the coil members across a respective center of the coil members is at least as large as a smallest dimension of the at least one opening of the housing perpendicular to the housing opening direction. In a suitable embodiment, a magnetic stray field generated by one of the two coil members can be compensated to a large extent by a magnetic stray field generated by the other of the two coil members, such that a magnetic field strength of a main magnet of the magnetic resonance rheology imaging system remains sufficiently unchanged so as to not affect magnetic resonance imaging.

In one embodiment, the transducer driving unit may comprise a function generator providing a sinusoidal output signal, and an amplifier to which the coil members are connectable.

Preferably, the one of the coil members is directly or indirectly mechanically linked to the piston in a region near the second end of the piston.

A small overall dimension of the housing and the piston in the direction parallel to the housing opening direction can readily be achieved if the windings of each of the two coil members are arranged in a planar way. The phrase "planar coil", as used in this application, shall in particular encompass coils having up to five layers of windings in the direction parallel to the housing opening direction. Preferably, the number of layers of windings in the direction parallel to the housing opening direction is up to and including three layers of windings, and, most preferable, each of the two coil members comprises only one layer of windings.

It another preferred embodiment, the first end of the piston is furnished with a curved surface. In this way, mechanical oscillations can effectively be applied to curved portions of the subject of interest. Preferably, the radius of curvature of the curved surface is adapted to a curvature of the curved portion of the subject of interest.

For an embodiment of the handheld oscillation applicator with the piston furnished with a curved surface, the windings of the two coil members may each be arranged on a curved surface. In this way, a small overall dimension of the housing and the piston in the direction parallel to the housing opening direction can be accomplished also in this case.

In one embodiment, the two coil members are identically designed. By that, the magnetic stray field generated by one of the two coil members can effectively be compensated by the magnetic stray field generated by the other of the two coil members. In another embodiment, the housing includes at least one ergonomically formed gripping member. By that, the operator can hold the oscillation applicator for a long time with little fatigue. Also, the operator can adjust the oscillation applicator in a more precise way.

In yet another embodiment, the handheld oscillation applicator further comprises at least one mechanical fastening member that is attachable to a component of the magnetic resonance rheology imaging system. In this way, the operator can have a convenient access to the handheld oscillation applicator, and the workflow can be improved.

Mechanical fastening member may comprise articulations, joints, spherical joints or hinges or other mechanical members that can provide a required freedom of movement for the oscillation applicator, and that appear suitable to the person skilled in the art.

If the mechanical fastening member further comprises at least one blocking member, a portion of the mechanical load that the operator has to take up while holding the handheld oscillation applicator can be diminished at least temporarily. This can in particular be advantageous in situations in which the interventionalist needs both hands for operating the intervention device.

It is another object of the invention to provide an oscillation applicator unit, including an embodiment of the disclosed handheld oscillation applicators or a combination thereof and a transducer driving unit for energizing the at least one transducer unit.

Furthermore, the oscillation applicator unit comprises a sensing unit, which is configured to determine a physical quantity that is representative of an amplitude of mechanical oscillations being applied to at least the portion of the subject of interest, and to provide an output signal representing the determined physical quantity.

Then, the oscillation applicator unit includes at least one electronic closed-loop control circuit for maintaining a mechanical displacement amplitude of the transducer unit at a selected level, wherein the closed-loop control circuit is configured to provide an output signal for controlling the transducer driving unit, based on the output signal received from the sensing unit.

In this way, mechanical oscillations of constant amplitude can be applied to at least a portion of the subject of interest, in particular in case of a movement of the handheld oscillation applicator, and a varying amplitude of the applied mechanical oscillations due to varying mechanical coupling between the handheld oscillation applicator and the subject of interest can be avoided or at least partially be corrected for.

In one embodiment, the sensing unit may comprise a pressure sensor, which may be attached to the first end of the piston, configured to be in contact with the subject of interest during applying mechanical oscillations, or it may be attached to the skin of the subject of interest.

In one embodiment, the sensing unit may comprise an accelerometer, which may for instance be designed as a micro-electromechanical system (MEMS).

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
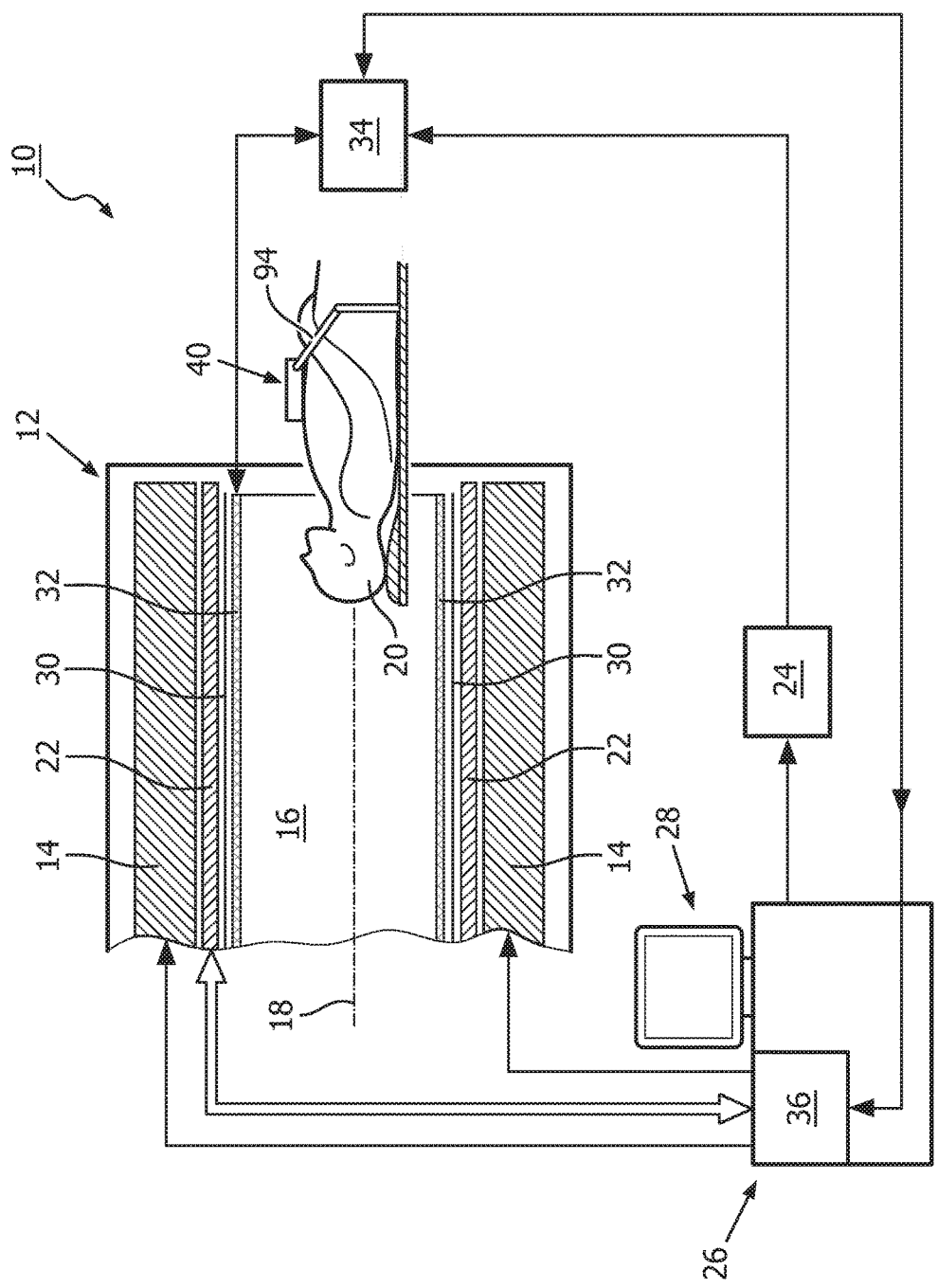
FIG. 1 illustrates a schematic partial illustration of a magnetic resonance rheology imaging system configured for magnetic resonance rheology application, with an embodiment of a handheld oscillation applicator in accordance with the invention.

FIG. 1 shows a schematic illustration of a part of an embodiment of a magnetic resonance rheology imaging system 10 configured for acquiring magnetic resonance signals from at least a portion of a subject of interest 20, usually a patient. The magnetic resonance rheology imaging system 10 comprises a scanning unit 12 having a main magnet 14. The main magnet 14 has a central bore that provides an examination space 16 around a center axis 18 for the subject of interest 20 to be positioned within, and is further configured for generating a static magnetic field $B_0$ at least in the examination space 16. For clarity reasons, a customary table for supporting the subject of interest 20 is only indicated in FIG. 1. The static magnetic field $B_0$ defines an axial direction of the examination space 16, aligned in parallel to the center axis 18. It is appreciated that the invention is also applicable to any other type of magnetic resonance rheology imaging system providing an examination region within a static magnetic field.

Further, the magnetic resonance rheology imaging system 10 comprises a magnetic gradient coil system 22 configured for generating gradient magnetic fields superimposed to the static magnetic field $B_0$. The magnetic gradient coil system 22 is concentrically arranged within the bore of the main magnet 14, as is known in the art.

The magnetic resonance rheology imaging system 10 comprises a control unit 26 provided to control functions of the scanning unit 12, the magnetic gradient coil system 22, and other functions of the magnetic resonance rheology imaging system 10. The control unit 26 includes a human interface device designed as a monitor unit having a touch-sensitive screen 28.

Furthermore, the magnetic resonance rheology imaging system 10 includes a radio frequency antenna device 32 designed as a whole-body coil that is provided for applying a radio frequency field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter unit 24 to the whole-body coil. The whole-body coil has a center axis and, in the operational state, is arranged concentrically within the bore of the main magnet 14 such that the center axis of the whole-body coil and the center axis 18 of the magnetic resonance rheology imaging system 10 coincide. As is common in the art, a cylindrical metal radio frequency shield 30 is arranged concentrically between the magnetic gradient coil system 22 and the whole-body coil.

The whole-body coil is also provided for receiving magnetic resonance signals during radio frequency receive phases from the nuclei of or within the portion of the subject of interest 20 that have been excited by the transmitted radio frequency field $B_1$. In an operational state of the magnetic resonance rheology imaging system 10, radio frequency transmit phases and radio frequency receive phases are taking place in a consecutive manner.

The radio frequency transmitter unit 24 is provided to feed radio frequency power of a magnetic resonance radio frequency to the whole-body coil via a radio frequency switching unit 34 during the radio frequency transmit phases. During the radio frequency receive phases, the radio frequency switching unit 34, controlled by the control unit 26, directs the magnetic resonance signals from the whole-body coil to an image processing unit 36 residing in the control unit 26. The image processing unit 36 is configured for processing acquired magnetic resonance signals to determine a magnetic resonance image of at least the portion of the subject of interest 20 from the acquired magnetic resonance signals. Many different variations of this technique are well known to the person skilled in the art, and thus need not be described in further detail herein.

In addition, the magnetic resonance rheology imaging system 10 includes an oscillation applicator system 38 (FIG. 4), which comprises a handheld oscillation applicator 40 with a transducer unit 48, a transducer driving unit 42 for energizing the transducer unit 48, a sensing unit 50, and a transducer control unit 52 with a closed-loop control circuit for controlling an amplitude of mechanical oscillations, as will be described later on.

Figure 2A:
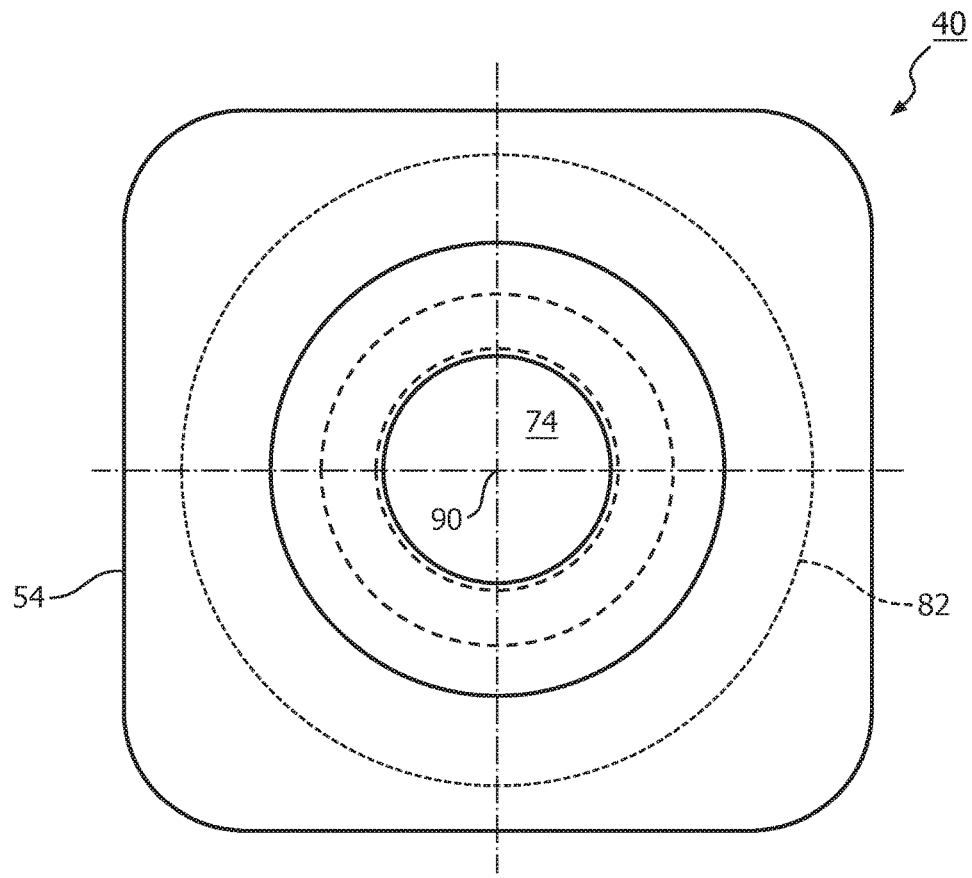
FIG. 2a is a schematic top view of the handheld oscillation applicator pursuant to FIG. 1.

The handheld oscillation applicator 40 (FIGS. 2a and 2b), upon activation, is configured for applying mechanical oscillations to at least the portion of the subject of interest 20 to be imaged by the magnetic resonance rheology imaging system 10.

To this end, the handheld oscillation applicator 40 includes a transducer unit 48 (FIG. 2b) that, upon being energized, is configured to output mechanical energy. The transducer unit 48 will be described in detail later on.

Figure 2B:
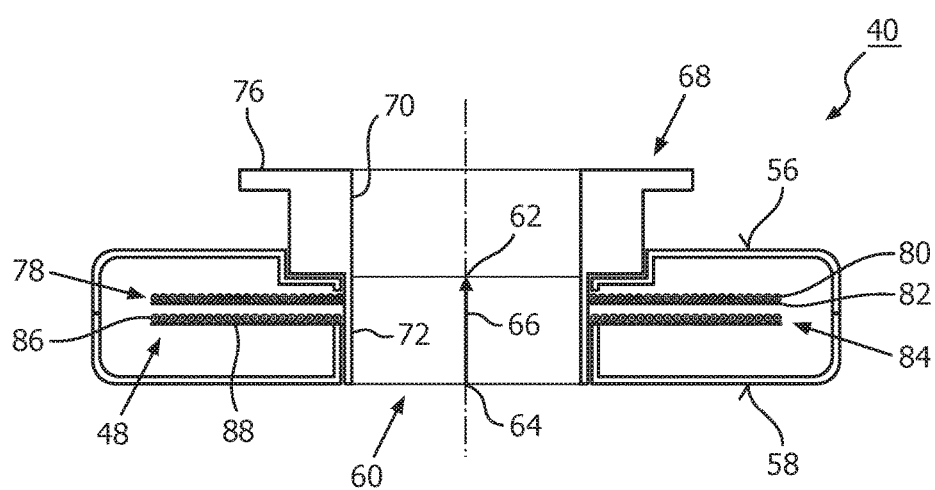
FIG. 2b shows a cross-sectional view of the handheld oscillation applicator pursuant to FIG. 2a, FIG. 3 depicts an alternative embodiment of a handheld oscillation applicator in accordance with the invention.

The handheld oscillation applicator 40 further comprises a housing 54 which includes a first surface 56 that is configured to be arranged proximal to at least the portion of the subject of interest 20 during applying mechanical oscillations, and at least a second surface 58 that is configured to be arranged distal to at least the portion of the subject of interest 20 during applying mechanical oscillations (FIG. 2b). The housing 54 comprises an opening 60 that extends between the first surface 56 and the second surface 58. A housing opening direction 66 is defined by a virtual connecting line between an opening center 62 of the opening 60 of the housing 54 at the first surface 56 and an opening center 64 of the opening 60 of the housing 54 at the second surface 58.

Moreover, the handheld oscillation applicator 40 includes a piston 68, which is mechanically linked to the transducer unit 48, and is configured to transfer at least a part of the mechanical energy of the transducer unit 48 to at least the portion of the subject of interest 20 to be imaged. The piston 68 comprises a first end 70 that is configured to be arranged proximal to at least the portion of the subject of interest 20 during applying mechanical oscillations, wherein the first end 70 of the piston 68 is configured to be closer to the subject of interest 20 than the first surface 56 of the housing 54, and a second end 72 that is configured to be arranged distal to at least the portion of the subject of interest 20 during applying mechanical oscillations.

Then, the piston 68 comprises an opening 74 that extends between the first end 70 and the second end 72. The opening 60 of the housing 54 and the opening 74 of the piston 68 at least partially overlap with regard to the housing opening direction 66, namely in that they completely overlap.

Both the opening 60 of the housing 54 and the opening 74 of the piston 68 have an elliptical cross-section, namely a circular cross-section of a diameter of about 35 millimeters.

Therefore, a dimension of the overlap of the opening 60 of the housing 54 and the opening 74 of the piston 68 perpendicular to the housing opening direction 66 in an operational state is 35 millimeters.

An overall dimension of the housing 54 and the piston 68 in the operational state in a direction parallel to the housing opening direction 66 is less than 35 millimeters.

In principle, as is appreciated by the one skilled in the art, other cross-sectional shapes for the opening 60 of the housing 54 and the opening 74 of the piston 68 are possible. For instance, a cross-sectional shape designed as a polygon, in particular a regular polygon, could be imagined.

Figure 4:
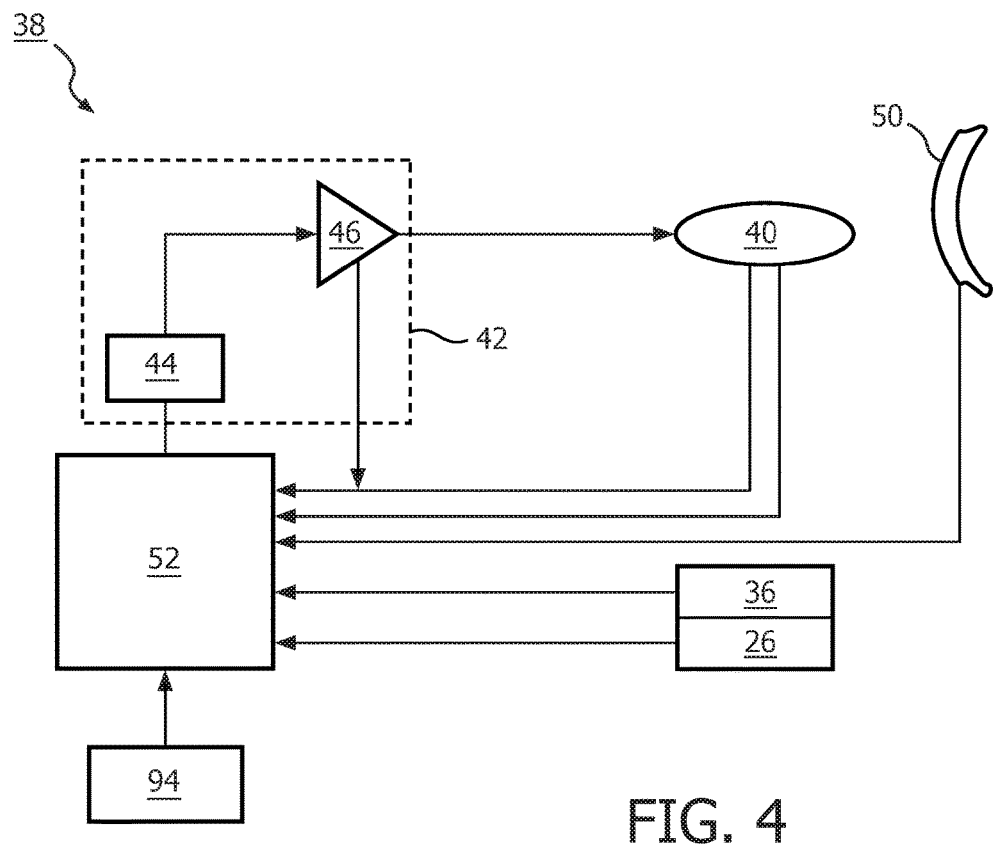
FIG. 4 shows a schematic diagram of an oscillation applicator system in accordance with the invention, and FIG. 5 schematically shows a prior art oscillation applicator in a perspective view.
Figure 5:
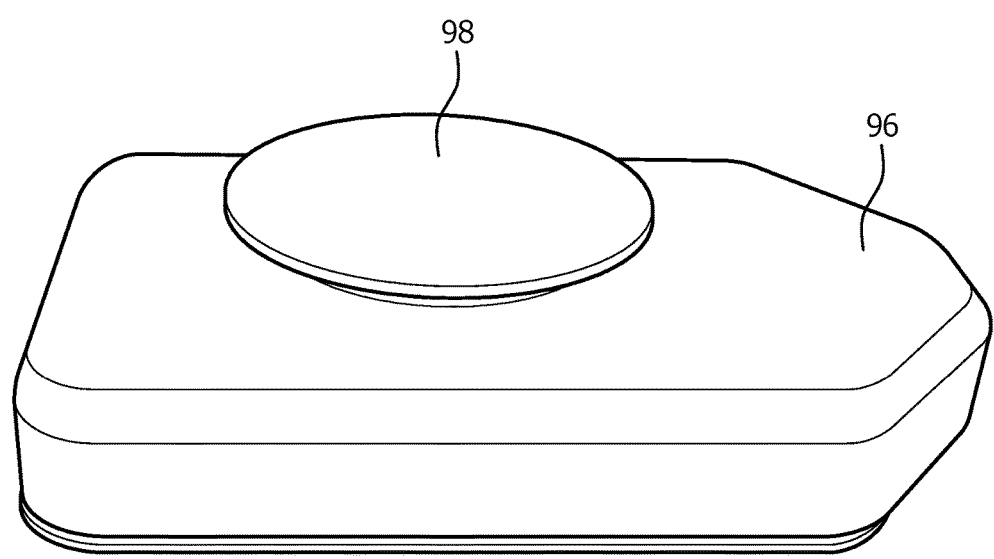

The transducer unit 48 comprises two coaxially arranged coil members 78, 84 having windings 80, 86 that are connected to the transducer driving unit 42 (not shown) for being provided with electrical energy. To this end, the transducer driving unit 42 includes a function generator 44 providing a sinusoidal output signal, and an amplifier 46 to which the coil members 78, 84 are connectable (FIG. 4). Going back to FIG. 2b, the two circular coil members 78, 84 are identically designed and each include a one layer winding 80, 86 of 200 turns designed as a flat spiral that is arranged on a surface of planar carrier 82, 88 with an inner diameter of about 37 millimeters and an outer diameter of about 97 millimeters. The planar carriers 82, 88 of the two circular coil members 78, 84 are arranged in parallel and perpendicular to the housing opening direction 66, with a gap of about 3 millimeters.

The coil member 78 that is arranged closer to the piston 68 is mechanically directly linked to the piston 68 by a plastic circular ring that is firmly attached to the second end 72 of the piston 68. The common axis of the coil members 78, 84 coincides with the housing opening direction 66, and a smallest distance between windings 80, 86 of each of the coil members 78, 84 across a respective center of the coil members 78, 84 is at least as large as a smallest dimension of the at least one opening 60 of the housing 54 in a direction perpendicular to the housing opening direction 66.

An electric current flows through the two coil members 78, 84, which are electrically connected in series, in opposite directions to the transducer driving unit 42. In this configuration, the magnetic stray fields generated by each of the two coil members 78, 84 cancel each other to a large extent, whereas a part of the component of the magnetic field generated by each of the two coil members 78, 84 remains that is arranged parallel to the direction of the common axis.

In an operational state, the handheld oscillation applicator 40 is hold by the interventionalist in a position such that the surfaces of the planar carriers 82, 88 of the two coil members 78, 84 are parallel to the magnetic field $B_0$ generated by the main magnet 14.

The piston 68 is positioned to touch the portion of the subject of interest 20 and, by that, is mechanically coupled to the subject of interest 20. For an improved mechanical coupling between the piston 68 and the subject of interest 20, the first end 70 of the piston 68 is designed as a circular ring flange 76 that extends radially from the housing opening direction 66 and has a planar surface lying in a plane that is arranged perpendicular to the housing opening direction 66.

The transducer unit 48 is driven by the transducer driving unit 42 at a frequency between 80 Hz and 100 Hz. By applying mechanical oscillations to the portion of the subject of interest 20, the handheld oscillation applicator 40 generates shear waves propagating within the tissue of the subject of interest 20. The frequency of the applied mechanical oscillations may as well be different from the disclosed range of 80 Hz to 100 Hz, and may be selected out of a range between 10 Hz and 1100 Hz, as is known in the art of magnet resonance rheology imaging.

The handheld oscillation applicator 40 is attached to the patient table by mechanical fastening members 94 designed as rods that are attached by a hinge and a spherical joint, respectively. The fastening members 94 make the handheld oscillation applicator 40 readily available to the interventionalist and support its positioning. Optionally, the mechanical fastening members 94 may include a blocking member to block any relative movement between the mechanical fastening members 94. Such blocking means are known to the person skilled in the art and do not have to be described in further detail herein.

The image processing unit 36 (FIG. 1) is, amongst other things, configured to image mechanical oscillations in the portion of the subject of interest 20 by processing the acquired magnetic resonance imaging data of at least the portion of the subject of interest 20 by applying a magnetic resonance imaging technique based on phase-contrast. By that, the magnetic resonance images show the propagating shear waves, and different types of tissue can clearly be distinguished by the different ways in which the shear waves propagate within the tissue.

The large overlap of the opening 60 of the housing 54 and the opening 74 of the piston 68 in the direction perpendicular to the housing opening direction 66 (FIGS. 2a and 2b) provides space for introducing an interventional device (not shown) through the openings 60, 74, while mechanical oscillations can be applied to at least the portion of the subject of interest 20 from all sides with respect to the introduced interventional device. The interventional device may be designed as a needle or one of the known catheter-type devices.

In this way, the handheld oscillation applicator 40 enables the interventionalist to operate an interventional device in a wide angular region with respect to the housing opening direction 66.

For an improved mechanical coupling between the piston 68 and a curved portion of the subject of interest 20, the first end 70 of the piston 68 could be designed as or furnished with a circular ring flange (not illustrated) that extends radially from the housing opening direction 66, and has a surface that is formed as a spherical segment of a sphere whose radius is adapted to a radius of curvature of the curved portion of the subject of interest 20. The surface of the circular ring flange can be either concave or convex.

In a suitable embodiment, the first end 70 of the piston 68 can be designed to take up one of interchangeable adapters that is selected by the interventionalist at his discretion as a best match to the portion of the subject of interest 20 to be imaged.

In another suitable embodiment (not illustrated) that is especially advantageous for curved portions of the subject of interest 20, the windings of the two coil members are each arranged on a surface of a curved carrier, which for example is designed as a spherical segment of a sphere. A radius of curvature of the sphere may be identical to that of the spherical segment surface of the first end of the piston.

Figure 3:
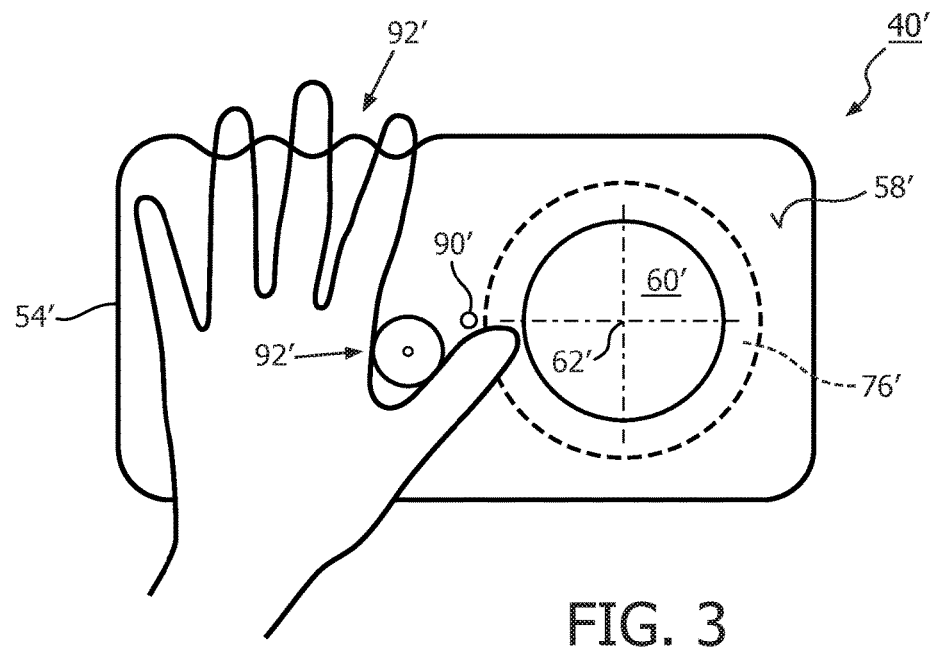

An alternative embodiment of a handheld oscillation applicator 40' is shown in FIG. 3. This handheld oscillation applicator 40' is distinct from the handheld oscillation applicator 40 pursuant to FIGS. 2a and 2b in that the opening center 62' of the opening 60' in the first surface 56' of the housing 54' is offset from a geometric center 90' of the first surface 56. As shown in FIG. 3, a larger portion of the second surface 58' of the housing 54' is available for the interventionalist to hold the oscillation applicator 40'. In order to facilitate the interventionalist holding the oscillation applicator 40' with little fatigue, and to support the interventionalist in adjusting the oscillation applicator 40' in a more precise way, the housing 54' includes two ergonomically formed gripping members 92' that are located at the larger portion of the second surface 58' of the housing 54'. The first ergonomically formed gripping member 92' is designed as three recessed grip members located in upper edge of the housing 54', in which three fingers of the interventionalist can rest. The second ergonomically formed gripping member 92' is designed as cone-like protrusion whose profile matches a shape of a hand in the region between thumb and index finger.

FIG. 4 shows a schematic diagram of the oscillation applicator system 38. The sensing unit 50 is designed as an accelerometer that is attached to the skin of the subject of interest 20. It is configured to determine an acceleration of a portion of the subject of interest 20 that is close to the region in which shear waves are being generated when the oscillation applicator 40 applies oscillations to the subject of interest 20. The determined acceleration is a physical quantity that is representative of an amplitude of mechanical oscillations being applied to at least a portion of the subject of interest 20 by the oscillation applicator 40. The sensing unit 50 provides an output signal indicative of the amplitude of mechanical oscillations as an input signal for a feedback control unit of the closed-loop control circuit of the transducer control unit 52.

Alternative or additional options of input signals for the feedback control unit are an electric current strength through the coil members 78, 84, a signal from a pressure sensor attached to the first end 70 of the piston 68, and data extracted from magnetic resonance imaging by the image processing unit 36 or from magnetic resonance navigators.

Based on the output signal received from the sensing unit 50, the feedback control unit provides an output signal for real-time controlling the transducer driving unit 42 so as to maintain a mechanical displacement amplitude of the transducer unit 48 at a level 94 selected or inputted by the interventionalist. In this way, a varying amplitude of the applied mechanical oscillations due to varying mechanical coupling between the handheld oscillation applicator 40 and the subject of interest 20 in case of a movement of the handheld oscillation applicator 40 or the subject of interest 20 can be corrected for.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

| REFERENCE SYMBOL LIST | |
|---|---|
| 10 | magnetic resonance rheology imaging system |
| 12 | scanning unit |
| 14 | main magnet |
| 16 | examination space |
| 18 | center axis |
| 20 | subject of interest |
| 22 | magnetic gradient coil system |
| 24 | radio frequency transmitter unit |
| 26 | control unit |
| 28 | touch-sensitive screen |
| 30 | radio frequency shield |
| 32 | radio frequency antenna device |
| 34 | radio frequency switching unit |
| 36 | image processing unit |
| 38 | oscillation applicator system |
| 40 | handheld oscillation applicator |
| 42 | transducer driving unit |
| 44 | function generator |
| 46 | amplifier |
| 48 | transducer unit |
| 50 | sensing unit |
| 52 | transducer control unit |
| 54 | housing |
| 56 | first surface |
| 58 | second surface |
| 60 | opening |
| 62 | center of the opening |
| 64 | center of the opening |
| 66 | housing opening direction |
| 68 | piston |
| 70 | first end |
| 72 | second end |
| 74 | opening |

REFERENCE SYMBOL LIST

| | |
|---|---|
| 76 | flange |
| 78 | coil member |
| 80 | winding |
| 82 | planar carrier |
| 84 | coil member |
| 86 | winding |
| 88 | planar carrier |
| 90 | geometric center |
| 92 | gripping member |
| 94 | fastening member |
| 96 | housing |
| 98 | piston |

The invention claimed is:

1. A handheld oscillation applicator for use in a magnetic resonance rheology imaging system, wherein the handheld oscillation applicator, upon activation, is configured for applying mechanical oscillations to at least a portion of a subject of interest to be imaged by the magnetic resonance rheology imaging system, the handheld oscillation applicator comprising a housing, including at least a first surface that is configured to be arranged proximal to at least the portion of the subject of interest during applying mechanical oscillations, and at least a second surface that is configured to be arranged distal to at least the portion of the subject of interest during applying mechanical oscillations, at least one transducer unit that, upon being energized, is configured to output mechanical energy, a piston, which is mechanically linked to the at least one transducer unit, and is configured to transfer at least a part of the mechanical energy of the at least one transducer unit to at least the portion of the subject of interest to be imaged, the piston comprising a first end that is configured to be arranged proximal to at least the portion of the subject of interest during applying mechanical oscillations, wherein the first end of the piston is configured to be closer to the subject of interest than the first surface of the housing, a second end that is configured to be arranged distal to at least the portion of the subject of interest during applying mechanical oscillations, and an opening that extends between the first end and the second end, wherein the housing comprises at least one opening extending between the first surface and the second surface, and wherein the at least one opening of the housing and the opening of the piston at least partially overlap with regard to a housing opening direction defined by a virtual connecting line between an opening center of the opening of the housing at the first surface and an opening center of the opening of the housing at the second surface and the openings of the housing and of the piston form through-going openings.

2. The handheld oscillation applicator as claimed in claim 1, wherein a dimension of the overlap of the at least one opening of the housing and the opening of the piston perpendicular to the housing opening direction is at least 30 millimeters.

3. The handheld oscillation applicator as claimed in claim 1, wherein an overall dimension of the housing and the piston in an operational state in a direction parallel to the housing opening direction is equal to or less than 45 millimeters.

4. The handheld oscillation applicator as claimed in claim 1, wherein at least one of the opening of the housing and the opening of the piston has an elliptical cross-section.

5. The handheld oscillation applicator as claimed in claim 1, wherein the center of the opening in the first surface of the housing is offset from a geometric center of the first surface.

6. The handheld oscillation applicator as claimed in claim 1, wherein the housing includes at least one ergonomically formed gripping member.

7. The handheld oscillation applicator as claimed in claim 1, wherein the at least one transducer unit comprises two coaxially arranged coil members having windings that are connectable to a transducer driving unit for being provided with electrical energy, wherein one of the coil members is directly or indirectly mechanically linked to the piston, the common axis of the coil members coincides with the housing opening direction, and a smallest distance between windings of each of the coil members across a respective center of the coil members is at least as large as a smallest dimension of the at least one opening of the housing in a direction perpendicular to the housing opening direction.

8. The handheld oscillation applicator as claimed in claim 7, wherein the windings of each of the two coil members are arranged in a planar way.

9. The handheld oscillation applicator as claimed in claim 7, wherein the two coil members are identically designed.

10. The handheld oscillation applicator as claimed in claim 7, wherein the first end of the piston is furnished with a curved surface.

11. The handheld oscillation applicator as claimed in claim 10, wherein the windings of the two coil members are each arranged on a curved surface.

12. The handheld oscillation applicator as claimed in claim 1, further comprising at least one mechanical fastening member.

13. The handheld oscillation applicator as claimed in claim 12, including several mechanical fastening members with at least one blocking member to block any relative movement between the mechanical fastening members.

14. An oscillation applicator system, including:
a handheld oscillation applicator according to claim 1, a transducer driving unit for energizing the at least one transducer unit, a sensing unit configured to determine a physical quantity that is representative of an amplitude of mechanical oscillations being applied to at least the portion of the subject of interest, and to provide an output signal representing the determined physical quantity, at least one electronic closed-loop control circuit for maintaining a mechanical displacement amplitude of the transducer unit at a selected level, wherein the closed-loop control circuit is configured to provide an output signal for controlling the transducer driving unit, based on the output signal received from the sensing unit.

* * * * *